(12) United States Patent
Eggers et al.

(10) Patent No.: US 7,569,053 B2
(45) Date of Patent: Aug. 4, 2009

(54) APPARATUS FOR RETRIEVING A TISSUE VOLUME WITH IMPROVED POSITIONING PRECURSOR ASSEMBLY

(75) Inventors: Philip E. Eggers, Dublin, OH (US); David Jacobs, Acton, MA (US)

(73) Assignee: Intact Medical Corporation

( * ) Notice: Subject to any disclaimer, the term of this patent is extended or adjusted under 35 U.S.C. 154(b) by 507 days.

(21) Appl. No.: 11/367,981

(22) Filed: Mar. 3, 2006

(65) Prior Publication Data
US 2007/0208338 A1 Sep. 6, 2007

(51) Int. Cl.
*A61B 18/14* (2006.01)
(52) U.S. Cl. .......................................... 606/45; 606/41
(58) Field of Classification Search ............. 606/32–50, 606/168, 170
See application file for complete search history.

(56) References Cited

U.S. PATENT DOCUMENTS

| | | | |
|---|---|---|---|
| 5,077,901 | A | 1/1992 | Warner et al. |
| 5,221,281 | A | 6/1993 | Klicek |
| 5,720,761 | A | 2/1998 | Kaali |
| 5,925,044 | A | 7/1999 | Hofmann et al. |
| 6,039,735 | A | 3/2000 | Greep |
| 6,056,764 | A | 5/2000 | Smith |
| 6,066,137 | A | 5/2000 | Greep |
| 6,277,083 | B1 | 8/2001 | Eggers et al. |
| 6,280,450 | B1 | 8/2001 | McGuckin, Jr. |
| 6,468,642 | B1 | 10/2002 | Bray et al. |
| 6,471,705 | B1 | 10/2002 | Biedermann et al. |
| 6,743,128 | B2 | 6/2004 | Liechty, II |
| 6,743,228 | B2 | 6/2004 | Lee et al. |
| 6,840,945 | B2 | 1/2005 | Manetakis et al. |
| 6,855,140 | B2 | 2/2005 | Albrecht et al. |
| 6,915,806 | B2 | 7/2005 | Pacek et al. |
| 7,044,956 | B2 * | 5/2006 | Vetter et al. .................. 606/167 |
| 7,229,440 | B2 * | 6/2007 | Ho et al. ........................ 606/47 |
| 2004/0006338 | A1 | 1/2004 | Vetter et al. |
| 2004/0006355 | A1 | 1/2004 | Vetter et al. |
| 2004/0087872 | A1 | 5/2004 | Anderson et al. |
| 2004/0097920 | A1 | 5/2004 | Desinger |
| 2004/0220564 | A1 | 11/2004 | Ho et al. |
| 2004/0255739 | A1 | 12/2004 | Clifford et al. |
| 2005/0027209 | A1 * | 2/2005 | Eggers ........................ 600/564 |

OTHER PUBLICATIONS

Surg Endosc (1994) 8:1076-1079 describes an electrosurgical laparoscopic trocar.

* cited by examiner

*Primary Examiner*—Michael Peffley
*Assistant Examiner*—Ronald J Hupczey, Jr.
(74) *Attorney, Agent, or Firm*—Mueller Smith & Okuley, LLC

(57) ABSTRACT

Apparatus for retrieving a tissue volume of a variety utilizing an electrosurgically excited cable implemented capture component which performs in combination with an improved precursor assembly. Where that assembly is electrosurgically excited, then it is located and dimensioned to avoid arc-over with the capture component cables. A precursor assembly also is implemented with electrically insulative ceramic blade and trocar configurations.

7 Claims, 10 Drawing Sheets

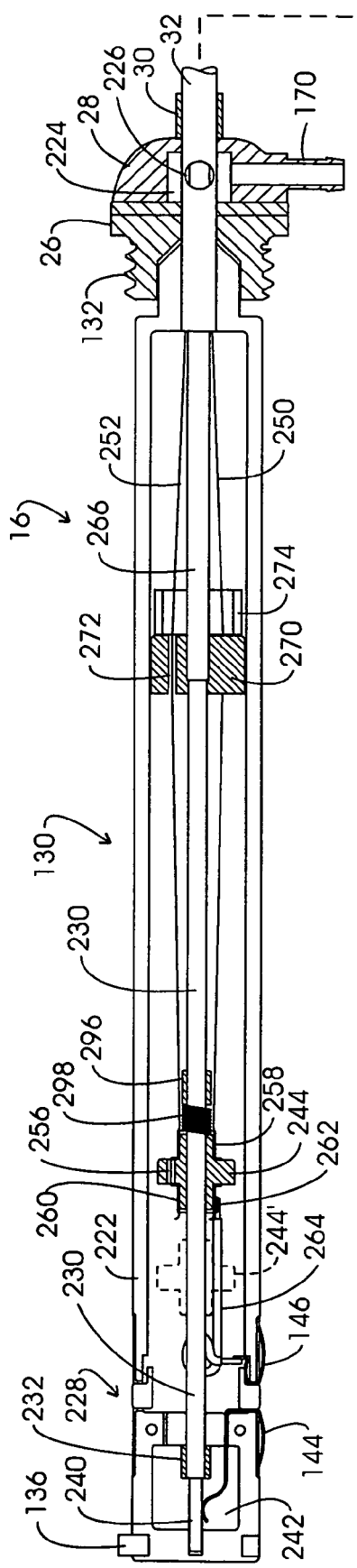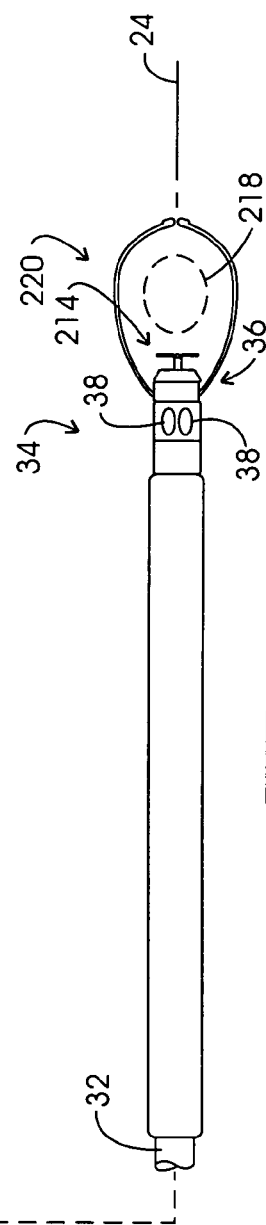
FIG. 4

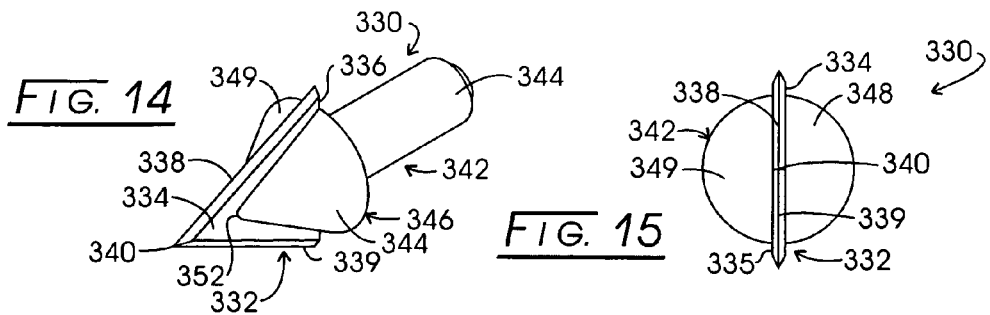
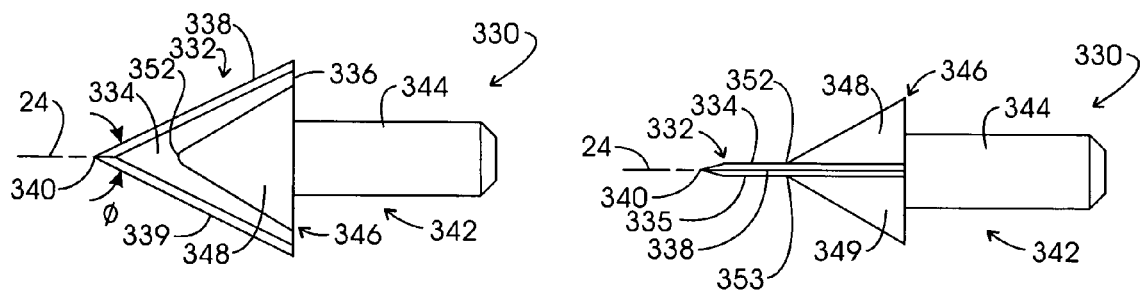
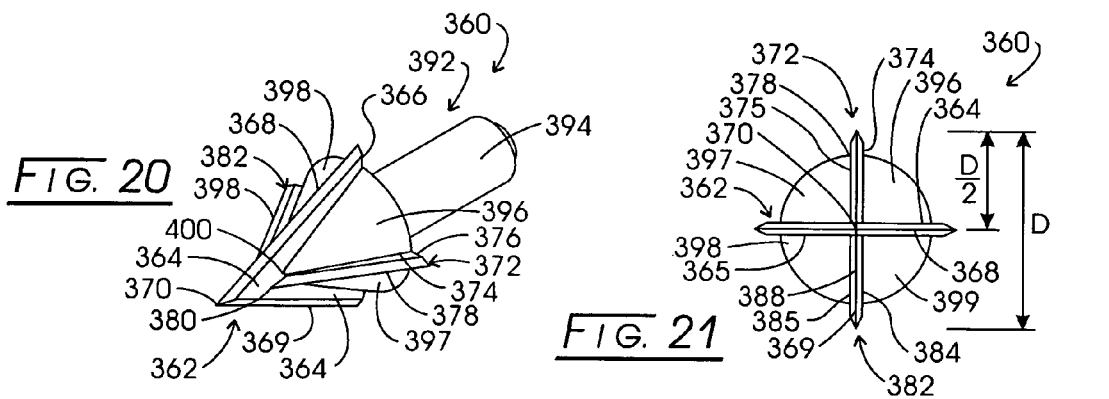
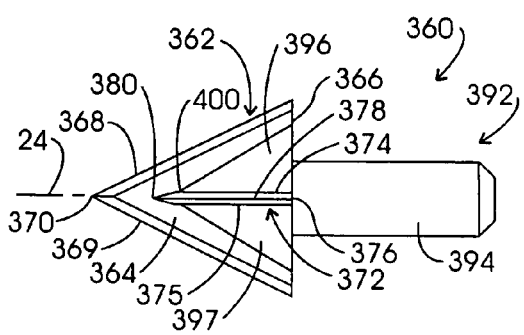
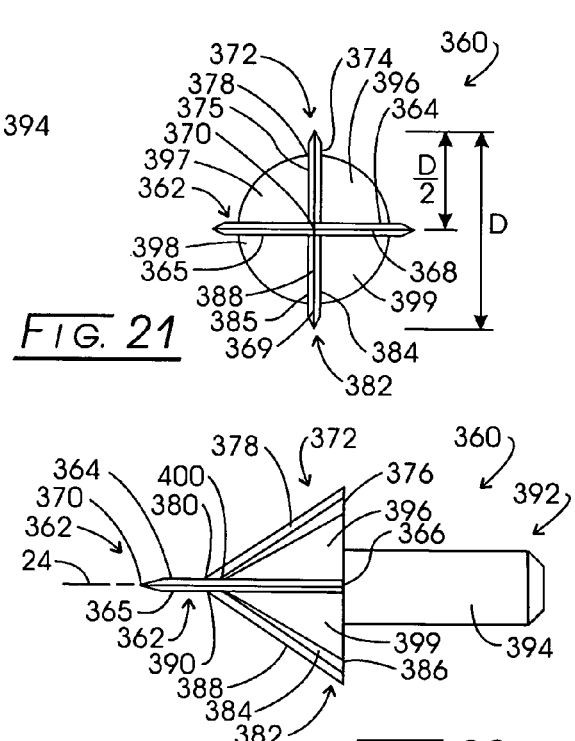

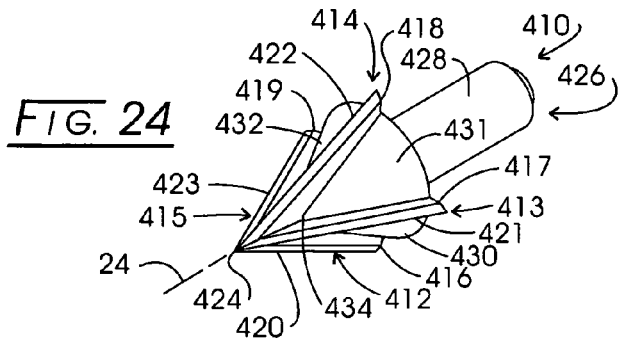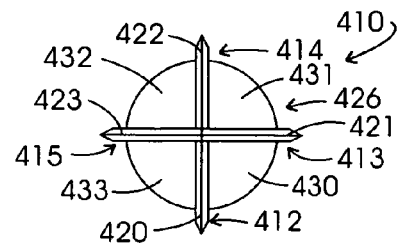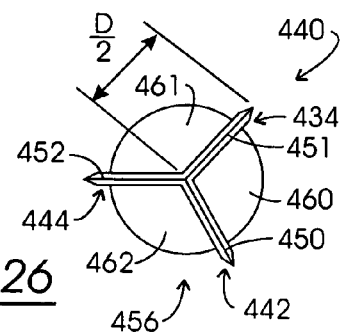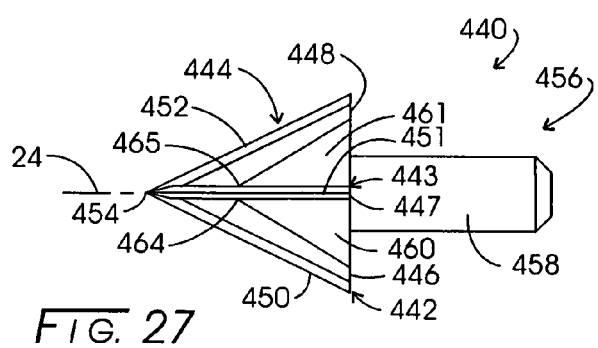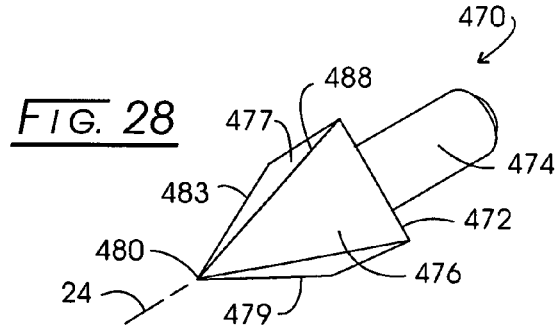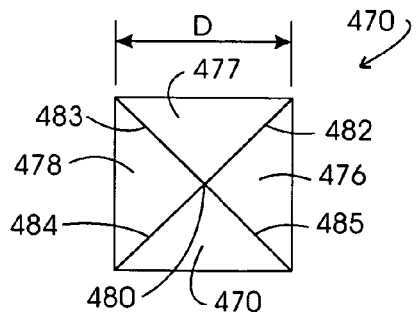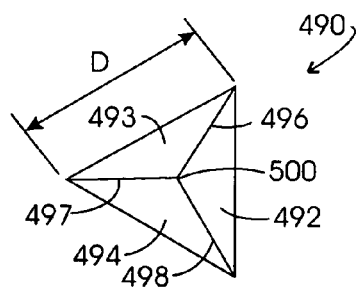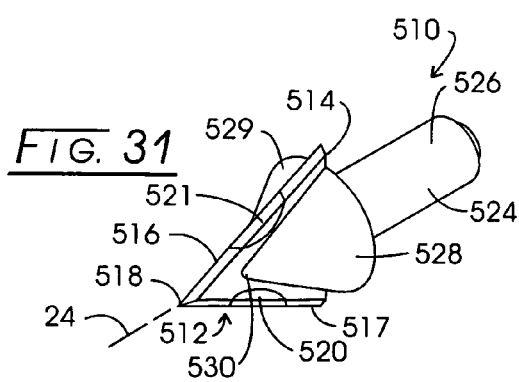

APPARATUS FOR RETRIEVING A TISSUE VOLUME WITH IMPROVED POSITIONING PRECURSOR ASSEMBLY

CROSS-REFERENCE TO RELATED APPLICATIONS

STATEMENT REGARDING FEDERALLY SPONSORED RESEARCH

Not applicable.

BACKGROUND OF THE INVENTION

The detection of tumorous lesions in the breast has progressed from early observation and palpation procedures to a variety of somewhat sophisticated imaging systems. A consequence of these advances in tumor detection is the identification of suspect tumor at an early stage in its development. Generally, at such early stages the suspect tumor may be somewhat small. Rather than resort immediately to an open surgical resection upon such early detection, practitioners generally carry out a preliminary, minimally invasive biopsy procedure. Such preliminary biopsy approaches are of importance, inasmuch as statistically, only 20% of these small tumors will be found to be malignant. Tumors determined to be benign have been left in situ with no excision. Over one million of these biopsies are performed in the United States each year, the procedure providing for the removal of part or all the suspect tissue for pathology examination and diagnosis. See generally:

(1) Rosen, Paul Peter, "Rosen's Breast Pathology", Lippincott-Raven Publishers, Philadelphia, 1997 pp 837-858.

One of the minimally invasive options is needle biopsy which may be either fine needle aspiration (FNA) or large core. Fine needle aspiration (FNA) is a procedure in which a fine needle, for example, of 21 to 23 gauge, having one of a number of tip configurations, such as the Chiba, Franzeen or Turner, is inserted into the breast and guided to the tumor site. A vacuum is created and the needle moved up and down along the tumor to assure that it collects targeted cellular material. Generally, three or more passes will be made to assure the collection of sufficient sample. Then, the needle and tissue sample are withdrawn from the breast for analysis.

The resulting specimen is subject to cytologic assay. In this regard, cell structure and related aspects are studied. This analysis has been used to improve or customize the selection of chemotherapeutic agents with respect to a particular patient.

While a fine needle aspiration biopsy has the advantage of being relatively simple, there are some drawbacks associated with its use. With fine needle aspiration, there remains a risk of false-negative results, which most often occur in cases involving extremely fibrotic tumor. In addition, after the procedure has been performed there may be insufficient specimen material for diagnosis. Finally, with fine needle aspiration alone the entire area of suspect tissue is not removed. Rather fragmented portions of tissue are withdrawn which do not allow a more advanced pathological investigation.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through a needle by vacuum suction. These needles have been combined with biopsy guns to provide automated insertion that makes the procedure shorter and partially eliminates location mistakes caused by human error or lesion displacement. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples. However, they still do not provide optimum pathological information. For further information concerning needle biopsy procedures see the following:

(2) Parker, Steve H, "Needle Selection and Steriotatic Large-Core Breast Biopsy", *Percutaneous Breast Biopsy* Eds. Parker, et al, Raven Press, New York, 1993 pp 7-14 and 61-79.

A device, which is somewhere between a needle biopsy and open surgery, is referred to as the Advanced Breast Biopsy Instrumentation (ABBI). With the ABBI procedure, the practitioner, guided by appropriate imaging, removes a core tissue sample of 5 mm to 20 mm in diameter. While the ABBI has the advantage of providing a large tissue sample similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for ABBI is limited by the size and location of the tumor, as well as by the presence of very dense parenchyma around the tumor. See the following publications:

(3) Parker, Steve H., "The Advanced Breast Biopsy Instrumentation: Another Trojan Horse?", Am. J. Radiology 1998; 171:51-53.

(4) D'Angelo, Philip C., et al., "Sterotatic Excisional Breast Biopsies Utilizing The Advanced Breast Biopsy Instrumentation System", Am. J. Surg. 1997; 174: 297-302.

(5) Ferzli, George S., et al., "Advanced Breast Biopsy Instrumentation: A Critique", J. Am. Coll. Surg., 1997; 185: 145-151.

Other biopsy approaches carry out a vacuum-assisted core biopsy wherein fragments of suspect tissue are removed with an 11-14 gauge needle-like instrument. One of these approaches is referred to as "Minimally Invasive Breast Biopsy" (MIBB). Another utilizes instrumentation marketed under the trade designation Mammotome® by Ethicon Endo-Surgery, Inc. of Cincinnati, Ohio. Those instruments, for instance, utilize an 8-11 gauge probe having a bladed tip for mechanically advancing the forward end of the probe into target tissue. When so located, tissue is vacuum drawn into a sample chamber, severed and removed for pathological evaluation. A similar device, marketed by Suros Surgical Systems, Inc. of Indianapolis, Ind. utilizes a trocar-like tip to mechanically advance the recovery probe into the target tissue. A substantial proportion of breast biopsies are carried out with such mechanical cutting or accessing approaches.

A minimally invasive approach to accessing breast lesions wherein the lesion is partially removed or removed in its entirety for diagnostic as well as therapeutic purposes has been described in U.S. Pat. No. 6,277,083 by Eggers, et al., entitled "Minimally Invasive Intact Recovery Of Tissue", issued Aug. 21, 2001. The instrument described includes a tubular delivery cannula of minimum outer diameter, the surgically sharp mechanical tip of which is positioned in confronting adjacency with a tissue volume to be removed.

Following such positioning, the electrosurgically excited leading edge of a capture component is extended forwardly from the instrument tip to enlarge while electrosurgically cutting and surrounding or encapsulating a tissue volume, severing it from adjacent tissue. Following such capture, the instrument and the encaptured tissue volume are removed through an incision of somewhat limited extent.

An improved design for this instrument, now marketed under the trade designation INTACT™ by Intact Medical Corporation of Natick, Mass., is described in U.S. Pat. No. 6,471,659 by Eggers, et al., entitled "Minimally Invasive Intact Recovery Of Tissue", issued Oct. 29, 2002. The INTACT™ instrumentation includes a tubular delivery cannula of minimum outer diameter, the tip of which is positioned in confronting adjacency with the target tissue volume to be removed. Such positioning is facilitated through the utilization of a forwardly disposed cruciform-shaped precursor electrosurgical electrode assembly. Located within the interior channel of this delivery cannula is a capture component configured with five relatively elongate and thin leafs which are mutually interconnected at their base to define a pentagonal cross-sectional configuration. Each of these leafs terminates forwardly at a tip region with a transversely bent forwardly extending eyelet structure. Slidably extending through each eyelet is an electrically conductive pursing cable of a pursing cable assembly. The tips additionally extend through a guidance assembly at the forward region of the delivery cannula. When the capture component is driven forwardly by the drive tube of a drive assembly, these leafs deploy outwardly and forwardly at an initial angle of attack of 35° to 45° while the pursing cables are "played out" and establish an electrosurgical cutting arc. Thus, cable movement defines a cutting profile that is extending outwardly at the noted 35° to 45° while moving forwardly to define an initial cutting profile extending circumferentially about the targeted tissue volume.

Drive imparted to the capture component from the drive tube is developed ultimately from an electric motor within the drive assembly. Each of the five pursing cables extends from the leading edge portion of the capture component through the delivery cannula to a cable terminator component which is pulled forwardly by the cable as the capture component forward portion moves from its initial position substantially within the interior channel of the delivery cannula toward an intermediate position wherein the electrosurgically excited leading edge leaf forward regions and associated pursing cables have achieved an effective maximum diametric extent. At this juncture, about one half of the targeted tissue volume will have been circumscribed by the capture component. At this position, the slidable cable terminator component will engage a cable stop component or collar. Forward movement of the attached cable assembly will be halted and a pursing action will ensue at the electrosurgical cutting leading edge wherein the tip regions of the cables are drawn inwardly with mutually inwardly directed angles of attack until the leaf tip portions converge at a capture position defining a capture basket configuration or tissue recovery cage substantially encapsulating the entire target tissue volume. As this position is reached, the tensioned cables permit no further movement and a stall condition is recognized at the drive motor to terminate electrosurgical excitation of the cable-defined leading edge of the capture component.

An advantageous feature of this form of drive assembly for the capture component resides in an arrangement where the noted cable stop component which engages the cable terminator component may be adjusted longitudinally to, in turn, vary the extent of the effective maximum diameter developed by the leading edge of the capture component. For example, the device can be configured to recover tissue specimens of 10 mm, 15 mm, 20 mm or greater effective maximum diametric extent. With the system, capture is positive, minimally invasive and the procedure is of short duration, for instance, requiring about 7 seconds to recover a 10 mm maximum effective diameter tissue sample. Accordingly, tissue samples may be extracted which may be larger than the diameter of the probe or cannula itself. Where such larger samples are extracted the cruciform-shape of the precursor assembly permits formation of a tissue access channel having a shape permitting substantial expansion of the channel effective circumference. Such a feature avoids excessive compression of the tissue sample as it is retrieved, a condition referred to as crush artifact.

Studies carried out with this recovery system have shown that instrument tip positioning is substantially facilitated utilizing the electrosurgically excited precursor assembly. However, its size and spacing from the capture component cables are important aspects of design for purposes of avoiding arc-over with one or more of the capture component cables. Such arc-over phenomenon may damage one or more of the cables and, without proper design, can be occasioned when the precursor electrode assembly is energized and the capture component cable is un-energized or vice versa.

Another approach avoiding the arc-over phenomena is through the utilization of an electrically insulative surgically sharp ceramic blade assembly for trocar-like implement. While practitioners are quite familiar with non-electrosurgical probe positioning, where larger tissue samples are to be removed, the resultant configuration of the formed tissue extraction channel should be contemplated with respect to the particular mechanical precursor chip employed.

BRIEF SUMMARY OF THE INVENTION

The present invention is addressed to apparatus for retrieving a target tissue volume of a variety employing a cable implemented deployable electrosurgical tissue capture component. That electrosurgically excitable component is combined at the forward region of the tissue retrieval instrument with improved precursor assemblies configured to prevent arc-over phenomena.

In an initial precursor assembly embodiment a cruciform electrosurgically energizable device is configured having straight electrodes with oppositely disposed outboard tips located perpendicularly from the instrument axis a distance less than the corresponding widthwise extent of the instrument forward region. These electrodes further are spaced forwardly from the capture component cables a distance effective to avoid arc-over phenomena with respect to them when the precursor electrodes are energized and the capture component cables are not.

The noted precursor electrode tips further are located to avoid arc-over phenomena when the capture component cables are deploying while electrosurgically energized and the precursor electrodes are not active.

In another embodiment the precursor assembly is configured as an electrically insulative ceramic blade with oppositely disposed surfaces exhibiting a triangular periphery symmetrically aligned with the instrument axis. The base portion of this triangular periphery is mounted to the instrument tip and from that base portion, two surgically sharp cutting edges extend to an axially aligned blade apex or point. Blade mounting is provided by a support assembly with electrically insulative tissue spreaders adjacent each blade surface which extend from the base in conical tapering fashion to spreader apexes located below the blade apex. This single blade precursor assembly can be configured with additional ceramic blades. For instance, two oppositely disposed ceramic blades having generally right triangular peripheries which are formed with oppositely disposed surfaces symmetrically aligned with the instrument axis may be added to the configuration in combination with a correspondingly modified electrically insulative tissue spreader. The secondary blades exhibit surgically sharp hypotenuse-related cutting edges which extend to secondary apexes located below the initial blade apex. Such an arrangement advantageously increases the incised pathway diameter, Di, from 0.64D to 1.27D, where, D is the effective diameter of the instrument tip.

These ceramic blades exhibiting a generally right triangular periphery may be combined to provide precursor assemblies with one to four such blades. With the arrangement, the blades provide hypotenuse-related surgical cutting edges extending from a base to a common blade apex. As before, the blades are combined with a supportive electrically insulative tissue spreader assemblage. Where three such blades are symmetrically disposed about an instrument or delivery member axis, an incised pathway diameter, Di, of 0.95D is realized.

The precursor assembly also may be provided as a trocar-like unitary solid electrically insulative cutting member formed of a ceramic material with a base supported at the instrument distal end. From this base, two or more surgically sharp edges extend to a tip. Where three such edges are provided, then the incised pathway diameter, Di, becomes 0.83D and where four such edges are provided, then the incised pathway diameter, Di, becomes 0.90D.

Other objects of the invention will, in part, be obvious and will, in part, appear hereinafter.

The invention, accordingly, comprises the apparatus possessing the construction, combination of elements, and arrangement of parts which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 4 is a partial sectional view of the instrument of FIG. 3 showing the orientation of components at a deployment of a capture component where leaf and associated drive features are at a completion of capture of a tissue volume;

FIG. 14 is a perspective view of a triangular shaped ceramic precursor assembly;

FIG. 15 is a front view of the assembly of FIG. 14;

FIG. 16 is a side view of the assembly of FIG. 14;

FIG. 17 is a top view of the assembly of FIG. 14;

FIG. 20 is a perspective view of a three bladed electrically insulative precursor assembly according to the invention;

FIG. 21 is a front view of the precursor assembly of FIG. 20;

FIG. 22 is a side view of the precursor assembly of FIG. 20;

FIG. 23 is a top view of the precursor assembly of FIG. 20;

FIG. 24 is a perspective view of another embodiment of an electrically insulative four bladed precursor assembly;

FIG. 25 is a front view of the precursor assembly of FIG. 24;

FIG. 26 is a front view of an electrically insulative three bladed precursor assembly;

FIG. 27 is a side view of the precursor assembly of FIG. 26;

FIG. 28 is a perspective view of a trocar-type precursor assembly having four sides;

FIG. 29 is a front view of the precursor assembly of FIG. 28;

FIG. 30 is a front view of a three sided electrically insulative trocar-type precursor assembly; and FIG. 31 is a perspective view of a precursor assembly incorporating an insulation coated metal surgically sharp cutting blade combined with electrosurgically energizable cutting edge regions.

DETAILED DESCRIPTION OF THE INVENTION

In the discourse to follow, precursor assemblies, as they are associated with electrosurgically excited capture components, are described. Initially, the structure of electrosurgically excited precursor electrodes themselves are addressed with respect to avoidance of the arc-over phenomena, following which mechanical, electrically insulated precursor assemblies are disclosed as they perform in conjunction with an electrosurgically excited capture component. In order to associate the dynamics of the capture component with respect to the precursor assemblies the discourse commences with a description of a preferred delivery assembly currently marketed under the trade designation INTACT™ by Intact Medical Corporation of Natick, Mass.

Figure 1:
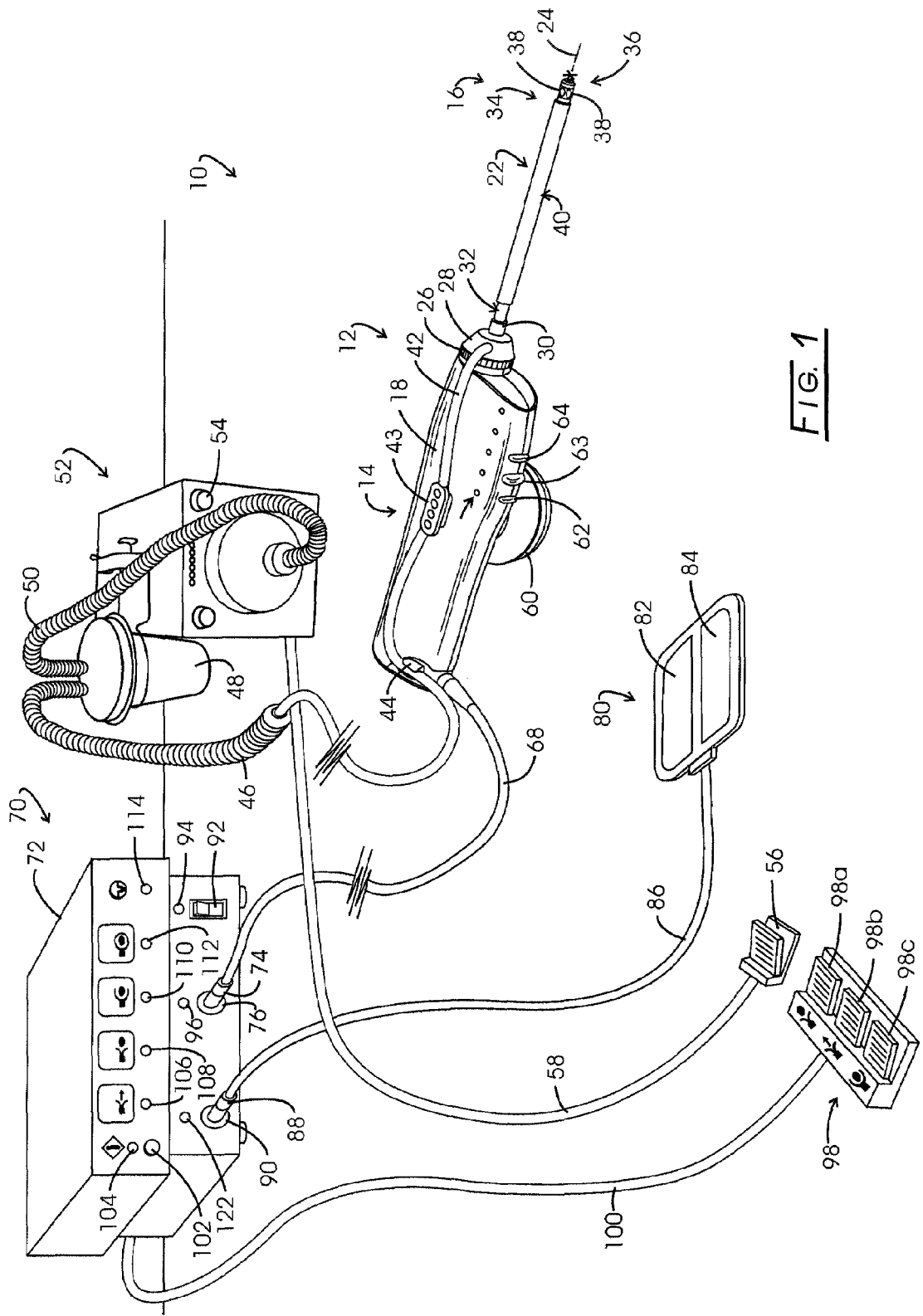
FIG. 1 is a perspective view of an electrosurgical system according to the invention.

Referring to FIG. 1, a system for isolating and retrieving a target tissue volume or biopsy sample is illustrated in general at 10. System 10 comprises a retrieval instrument or delivery assembly represented generally at 12 which includes a reusable component represented generally at 14, sometimes referred to as a "handle". Instrument 12 additionally includes a disposable delivery member represented generally at 16, the rearward portion of which is removably mounted within the polymeric housing 18 of reusable component 14. The delivery member or disposable component 16 is sometimes referred to as a "probe".

Delivery member 16 includes an elongate cannula assembly represented generally at 22 which extends along and is symmetrically disposed about an instrument axis 24. The proximal portion of cannula assembly 22 extends through a rotatable, externally threaded connector 26. Connector 26, in turn, is threadably engaged within housing 18. Cannula assembly 22 additionally extends through a rotatable suction manifold 28 which is a component of an evacuation system. Manifold 28 is retained in position on cannula assembly 22 by a ferrule or collar 30 which is mounted over the exterior or outward surface of a tubular cannula component, a portion of which is represented at 32. Most of the surface of the cannula assembly 22 will be seen to be covered with an electrically insulative thin polymeric shrink-wrap or tube. The forward region of the cannula assembly 22, as represented generally at 34 extends to a distal end or tip represented generally at 36. Suction or vacuum manifold 28 is in vacuum conveying and fluid receiving relationship through cannula assembly 22 with four intake ports located at forward region 34, two of which are shown at 38. The evacuated fluids will be at an elevated temperature due to the electrosurgical nature of the instrument 12 and will include steam, smoke and liquid such as blood and accumulations of local anesthetic. Accordingly, a thermally insulative sleeve 40 is positioned over cannula component 32 to protect patient tissue from thermal damage. Vacuum is conveyed to and this elevated temperature fluid is received from suction manifold 28 via a flexible transparent polymeric tube 42. Tube 42 extends from an evacuation outlet (not shown) at manifold 28 into press-fit connection with the connectors 43 and 44, whereupon it is coupled with a flexible tube or hose of larger diametric extent shown at 46. Hose 46 extends to a fluid trap and filter assemblage 48 which is in vacuum communication via flexible hose 50 with the suction input of a suction pump assembly represented generally at 52. Vacuum or suction pump assembly 52 may be of a type marketed under the trade designation "Versa Vac 2" by Stackhouse, Inc. of Palm Springs, Calif. Pump assembly 52 may be actuated into operation from a switch arrangement shown at 54 or through the utilization of a footswitch 56 coupled to the pump assembly 52 via a cable 58.

Connectors as at 43 are positioned on each side of the housing 18 and function additionally to support a stabilizer hand grip, for example, the annulus-shaped grip represented at 60. Connectors as at 43 also may be employed to support the instrument 12 or stereotactic manipulation. Positioned at the forward portion of housing 18 are three button switches 62-64 which function respectively as an arm/disarm switch; an energize/position switch; and a start tissue capture switch. Immediately above the switches 62-64 on each side of housing 18 are linear arrays of light emitting diode (LED) based indicator or cueing lights, one such array being represented generally at 66. The visual cues provided by the indicators at array 66, from the forward region of housing 18 toward the rear region thereof, provide a start/reset cue as a green light; a tissue capture complete cue provided as a green light; a start tissue capture cue (above switch 64) provided as a yellow light; an energize/position cue (above switch 63) provided as a yellow light; and an arm/disarm cue (above switch 62) provided as a green light. Energization and electrical control is provided to the instrument 12 via a multi-lead cable 68 which connects with a combined control assembly and electrosurgical generator represented generally at 70 and incorporated within a console 72. The control assembly function performs in conjunction with control assembly counterparts incorporated within instrument 12 and principally within reusable component 14. Device 70 is provided as a model "3000 RF Controller" marketed by Intact Medical Corporation (supra). Connection of the cable 68 with the console 72 is shown as a multi-lead connector 74 which is coupled to a console connector 76. The electrosurgically active electrode assembly of the instrument 12 performs in mono polar fashion. Thus, a conventional, relatively large dispersive return electrode assembly, as shown in general at 80, is positioned against the skin surface of the patient. Assembly 80 is configured as having two electrode components 82 and 84 which are connected via cable 86 and connector 88 to console connector 90. Power is supplied to the circuitry at console 72 upon actuation of an on/off switch 92. When switch 92 is in an "on" orientation, a green visual indicator LED 94 located above the switch is energized. Proper connection of the cable 68 and connector 74 with console connector 76 is indicated by an illuminated green LED 96 positioned above connector 76. This connection test is carried out by directing current to a coding resistor within housing 18. A three-pedal foot switch represented generally at 98 is coupled via a cable 100 to the rear panel of console 72. The three-pedals, 98a,-98c of switch 98 emulate and provides alternative switching with respect to button switches 62-64.

Visual cueing corresponding with that at housing 18 LED arrays as at 66 also is provided at console 72. In this regard, a start/reset switch 102 is operationally associated with an LED indicator 104 which illuminates in a green color upon actuation of that switch. An energize/position mode visual cue LED representing an energization of a precursor electrode assembly at tip 36 is shown at 106. This LED provides a yellow output during the electrosurgical advancement of cannula assembly tip 36 into confronting adjacency with a targeted tissue volume. It should be noted that the electrosurgical implementation of the precursor assembly represents one approach. However, as will be described later herein, an electrically insulative precursor blade as well as trocar assembly also will be described. As a next visual cueing, a green, arm/capture mode visual cue is provided by an LED 108 to represent an arming of the tissue capture feature of instrument 12. Once an arm/disarm switch as at 62 or 98a is depressed, the energize/position switches as at 63 or 98b are no longer activatable. However, the practitioner may return to the positioning mode by again depressing an arm/disarm switch. To enter a capture mode, the practitioner depresses the foot switch 98c or capture switch 64. A yellow capture mode visual cue is provided by an LED 110 to represent the start of and carrying out of a tissue capture or retrieval procedure and upon completion of such capture, a green capture complete visual cue is provided by a green LED 112. A pause mode condition is represented by the energization of a green LED 114. In general, the pause mode is entered during a procedure by releasing capture switch 64 or foot switch 98c. When in a pause mode, the active capture electrodes of the instrument 12 are not energized and deployment of its capture component is halted. However, the evacuation function carried out by the suction pump assembly 52 continues to perform. To reenter the capture mode, the practitioner again depresses foot switch 98c or capture switch 64. Upon such re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids may, for example, be accumulations of local anesthetic solution, blood or the like.

An assurance that the vacuum system is operating, at least to the extent that the vacuum pump assembly 52 is active, can be accomplished with a vacuum actuated switch (not shown) attached with the conduiting extending between the pump assembly 52 and the instrument 12. For example, unless such a switch is actuated, the commencement of a procedure can be logically blocked by the control assembly 70. In addition to the removal of smoke and such fluids as are discussed above, the evacuation system including pump assembly 52, conduiting defining a transfer channel extending to the intake ports 38, functions to remove steam which is generated by the encounter of an electrosurgical cutting arc with fluid of tissue cells. This removal of steam (as a component of elevated temperature fluid) serves, inter alia, to protect healthy tissue surrounding the region of cutting from thermal trauma.

At the time the connector 88 of return electrode 80 is coupled to console connector 90 and switch 92 is in a power-on condition, a patient circuit safety monitor (PCSM) carries out a self test. On subsequent actuation of the start/reset switch 102, a fault test with respect to the two electrode components 82 and 84 is performed. In the event the latter test fails, then both visual and aural pulsating warning cues are activated, the visual cue being provided at a red LED 122 located adjacent connector 90.

Figure 2:
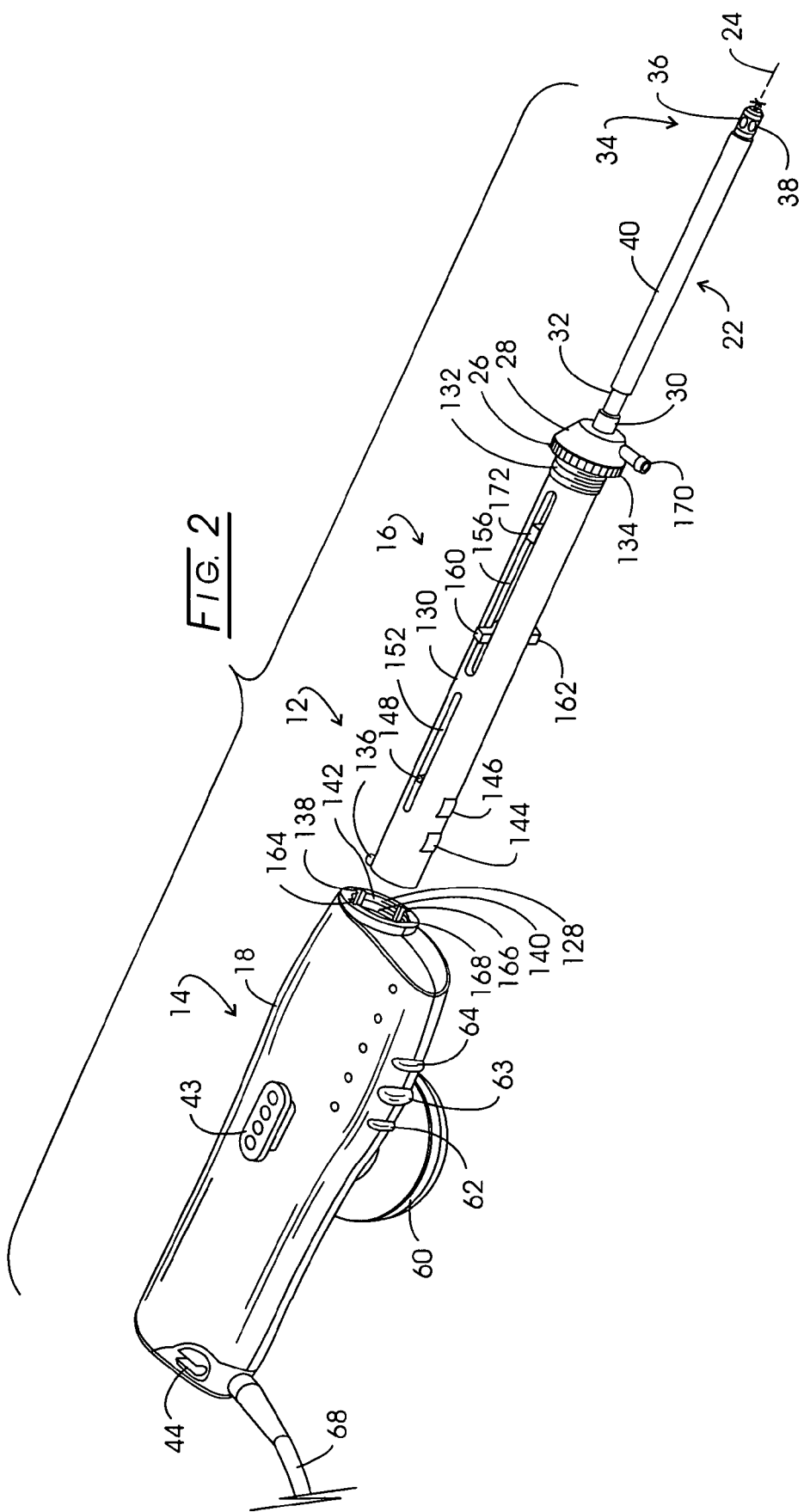
FIG. 2 is an exploded view of an electrosurgical instrument shown in FIG. 1.

Referring to FIG. 2, the disposable component 16 of instrument 12 is revealed in an orientation prior to its insertion within the housing 18 of reusable component 14. In the figure, cannula assembly 22 is seen extending forwardly from a cylindrically-shaped support housing 130. The forward region of support housing 130 supports the rotatable connector 26. In this regard, it may be observed that the connector 26 is configured with external threads 132 which are affixed for rotation with a grasping surface 134 formed with spaced indentations to facilitate its hand rotation. At the rearward end of support housing 130 there is located an upstanding indexing pin 136 which, during installation of the disposable component 16, is slidably received within an upwardly disposed elongate slot 138 extending internally along an elongate receiving cavity 140. The forward end of receiving cavity 140 of housing 18 is formed with an alignment bushing 128. Alignment bushing 128 is configured with internal threads 142. Internal threads 142 of alignment bushing 128 within cavity 140 threadably engage the external threads 132 of connector 26 when the disposable component 16 is mounted with the reusable component 14.

Positioned opposite indexing pin 136 on support housing 130 are two, spaced apart electrical contacts 144 and 146 which are oriented to make wiping contact with corresponding electrical terminals disposed within housing 18 upon the insertion of support housing within the receiving cavity 140. Contacts 144 and 146 selectively receive electrosurgical cutting current which is applied respectively to a precursor electrode assembly at tip 36 and the electrosurgical cutting and pursing cables associated with a capture component initially retained within cannula assembly 22. Those pursing cables extend from the capture component within cannula component 32 to a cable terminator component having guidance tabs or ears, one of which is revealed at 148 slidably mounted within an elongate stabilizer slot 152 arranged in parallel with axis 24. A corresponding guidance tab and slot combination is found at the opposite side of supporting housing 130. Located forwardly of the slots as at 152 are two elongate drive slots, one of which is shown at 156 similarly arranged in parallel with axis 24. The outwardly extending ears or guide tabs of a drive assembly drive member extend from these slots and are seen at 160 and 162. These ears or tabs 160 and 162 support rearwardly disposed driven surfaces which are used to impart forward movement to the drive assembly component. This forward movement functions to deploy the noted capture component from cannula component 132. When the support housing 130 is installed within the receiving cavity 140 of housing 18, these tabs 160 and 162 pass through oppositely disposed notches shown respectively at 164 and 166 provided at a forward portion of housing 18 as part of alignment bushing 128. Similarly, a notch 168 is located forwardly within housing 18 to permit passage of the electrical terminal 144 and 146. Alignment bushing 128 is configured to form the forward portion of the elongate slot 138 and notch 168.

The procedure for installing the disposable component 16 within reusable component 14 involves the sliding of support housing 130 within the receiving cavity 140 and rotating grasping surface 134 of connector 26 to provide for the engagement of threads 132 with threads 142. Upon completing the assembly, the flexible, transparent tube 42 of the evacuation assembly may be attached to an evacuation outlet 170 depending outwardly and in fluid and suction or vacuum communication with suction manifold 28. Finally, a tab as at 172 is seen extended through a forward portion of the drive slot 156. This tab may be a component above a drive assembly providing a positive blocking or stop limiting the extent of forward travel permitted by the drive member component having the ears 160 and 162. It is located in accordance with a pre-selected capture component maximum effective diametric extent. When the stop function is carried out a capture complete signal is derived as a current spike witnessed upon a stall of an electric drive motor. That signal is conveyed to control assembly 70.

Figure 3:
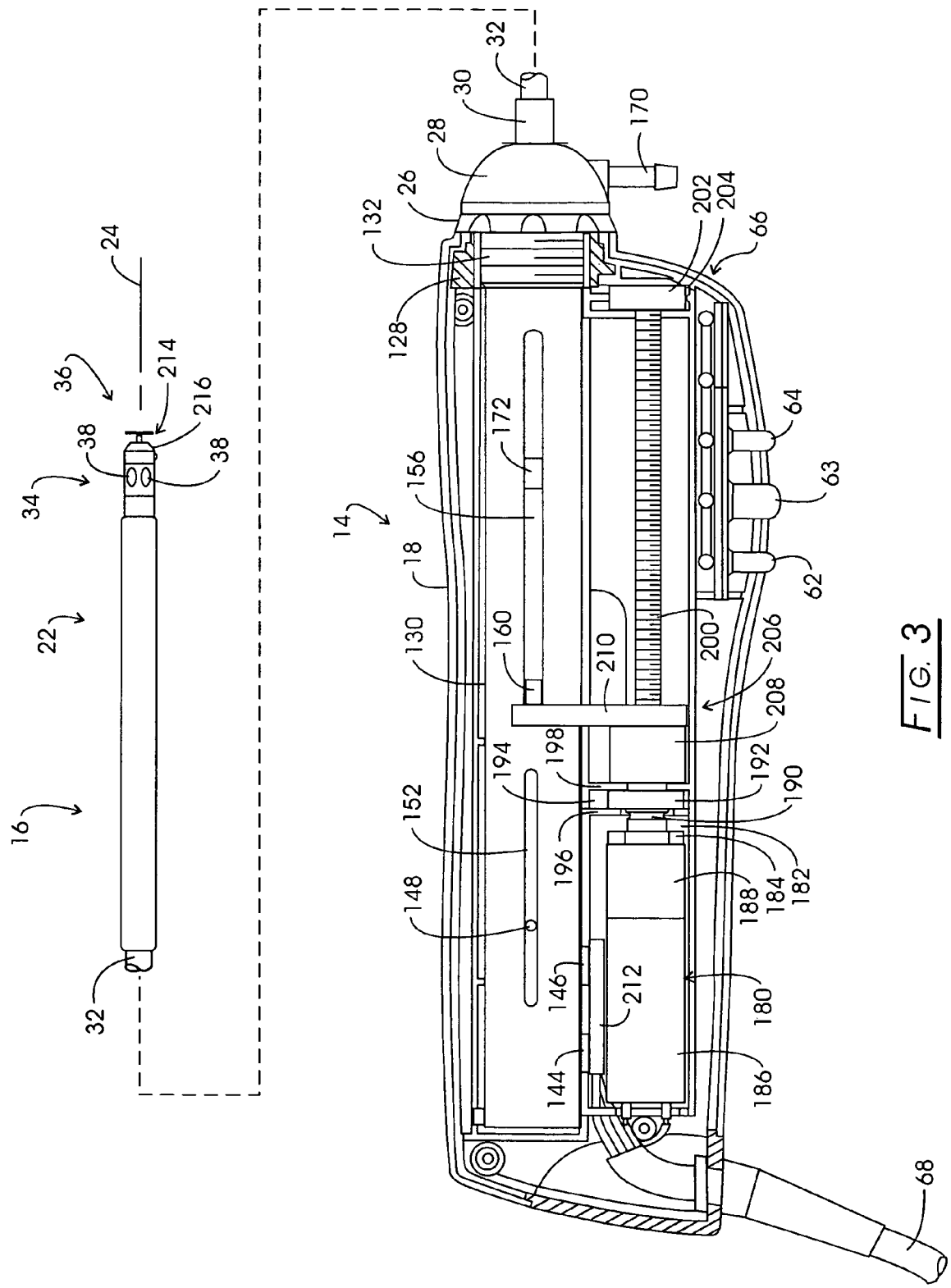
FIG. 3 is a partial sectional view of the instrument shown in FIG. 2 with portions broken away.

Referring to FIG. 3, a sectional view is presented illustrating the operative association of motor drive features of the reusable component 14 with the support housing 130 of disposable component 16. In the figure, a motor assembly represented generally at 180 is seen to be located within a motor mount chamber 182. In that chamber 182 the motor assembly 180 is permitted some self-aligning movement but is restrained from rotational movement by a torque stop component 184. Assembly 180 incorporates a motor component 186 which is coupled in driving relationship with a planetary gear assembly 188. The drive output of the planetary gear assembly 188 is connected in driving relationship with a stainless steel flexible bellows-shaped coupler 190 which extends through a fluid seal 192 located within a seal chamber 194 defined by oppositely disposed and spaced apart bulkheads 196 and 198. Seal 192 does not constrain the coupler 190 and permits the noted self-alignment of motor assembly 180 with respect to its coupling to a rearward end of an elongate threaded translation component 200. The forward end of translation component 200 extends into engagement with a thrust bearing 202. Bearing 202 provides support against all of the driving forces imposed from the motor assembly 180 and is mounted and secured within a thrust bearing chamber 204. Translation component 200 is threadably engaged with a transfer assembly represented generally at 206 which comprises a ball screw or nut component 208 and a generally Y-shaped yoke 210 which is configured to extend to a position aligned for driving but freely abutting engagement with the tabs or ears 160 and 162 (FIG. 2). During the capture procedure, the translation component 200 is drivably rotated in an appropriate direction to move the transfer assembly 206 forwardly. That movement, in turn, urges a drive component forwardly until capture component pursing activity is completed and the motor component 186 enters a stall condition. At that juncture, the control system 70 halts electrosurgical cutting current and reverses the directional drive sense of motor 186 to cause the transfer assembly 206 to return to a "home" position generally illustrated in the instant figure. The figure additionally reveals that the two electrical contacts 144 and 146 located upon support housing 130 will be in contact with corresponding contacts (not shown) supported by a polymeric contact clamp 212.

FIG. 3 also reveals some details of the tip 36 of the cannula assembly 22. For the instant embodiment, the tip incorporates four straight generally L-shaped precursor electrode components arranged in a cruciform shape or symmetrically about instrument axis 24 as is represented in general at 214. The electrode components of the precursor assembly 214 will be seen to be spaced forwardly of a truncated cone-shaped ceramic (alumina) protective tip component 216. Tip component 216 functions to provide an arc-resistant or arc isolating tip portion preventing its breakdown. For this electrosurgical embodiment of the precursor assembly, the geometry of the electrode components as well as their spacing is selected for the purpose of avoiding arc-over in conjunction with the leading edge of the capture component.

The present invention is concerned initially with the avoidance of arc-over between precursor assembly 214 and the leading electrosurgical cutting cable of a capture component as it deploys. Thus, the features of that deployment mechanism are considered. In this regard, looking to FIG. 4 the orientation of the deployment drive components is revealed in connection with a full capture of a target tissue symbolically indicated at 218. In association with a schematically illustrated fully pursed capture component represented generally at 220. Note in the figure that the forward surface of the precursor electrode assembly has been located in confronting relationship with target tissue 218 but resides in surrounding tissue as opposed to the target itself. The sectional view of support housing 130 shows that it is formed from two identical moldings, one being shown at 222. These paired moldings are retained together adhesively as well as forwardly by connector 26 which, additionally supports cannula component 32. Component 32 extends through an evacuation chamber 224 formed within manifold 28. Vacuum communication with the chamber 224 is provided by a port or opening 226 in component 32.

Extending from adhesive attachment at a rearward bulkhead represented generally at 228 defined by the paired molding components is the inward portion of a support tube 230. Tube 230 is anchored at the rearward side of bulkhead 228 by a plastic collar 232 and extends forwardly to the forward region 34. Insulatively extending through the interior of the support tube 230 is a precursor electrode tube 240 which is in physical and electrical contact with the precursor assembly 214. The rear tip of tip 240 extends along axis 24 into engagement with the paired molding components at a cavity 242. That portion of the precursor electrode tube 240 which extends rearwardly from support tube 230 is configured with an electrically conductive surface which receives precursor electrode current through resiliently biased terminal component 144.

Five braided stainless steel cables extend from their connection with the capture component 220 to a polymeric cable terminator component 244 which is slidably mounted over support tube 230 and is moveable thereon in parallel with the instrument axis 24. Two of the braided pursing cables are stylistically represented in the drawing at 250 and 252. However, all five of these cables extend to and are connected with the cable terminator component 244. Component 244 is formed with five longitudinally disposed and radially spaced channels into each of which one of the cables 250-254 extend (see FIGS. 5 and 6). In the figure, cable 252 is seen extending through a channel 256. All five cables are retained or fixed to the terminator component 244 by two stainless steel collars. In this regard, a forward stainless steel collar or ferrule is shown at 258 while a rearward one is shown at 260. Collar 260 additionally functions to apply electrosurgical cutting power or current simultaneously to all five of the pursing cables and, accordingly, it initially is nickel plated and then gold plated such that the electrosurgical cutting current may be applied to it through a solder union 262. Union 262 connects the collar 260 with a multi-strand and highly flexible insulated copper cable 264. Cable 264, in turn, is soldered (or welded) to the forward electrical terminal assembly 146. Terminator component 244 is stabilized for slidable movement by two outwardly extending guide tabs or ears, one of which has been described at 148 in conjunction with slot 152 in FIGS. 2 and 3. With this arrangement, as the five cables are electrically excited with electrosurgical cutting current, they are drawn in tension forwardly to, in turn, pull the terminator component from its initial position shown in phantom at 244' in slidable fashion forwardly over the support tube 230.

Drive is imparted to the five somewhat elongate leafs of capture component 220 from a drive tube 266 which, as described in connection with FIG. 3, is, in turn, driven from its outwardly disposed drive ears or tabs 160 and 162. These tabs extend through slots, one of which is shown at 156 in FIG. 3. The drive member associated with these tabs is shown in FIG. 4 at 270 in its capture complete orientation. Member 270 is attached to drive tube 266 which is slidably mounted over support tube 230. As drive member 270 is driven forwardly from its initial position (not shown) the five pursing cables 250-254 pass through it via five channels. One such channel is stylistically represented in the figure at 272 in connection with cable 252. These cables additionally slide over a capture stop component 274 which is mounted to the housing 130 paired components. Stop 274 is fixed in place in conjunction with earlier-described tab 172 (FIG. 2). The drive member 270 will have abuttably contacted stop member 274 at the completion of pursing capture as represented in this figure.

Figure 5:
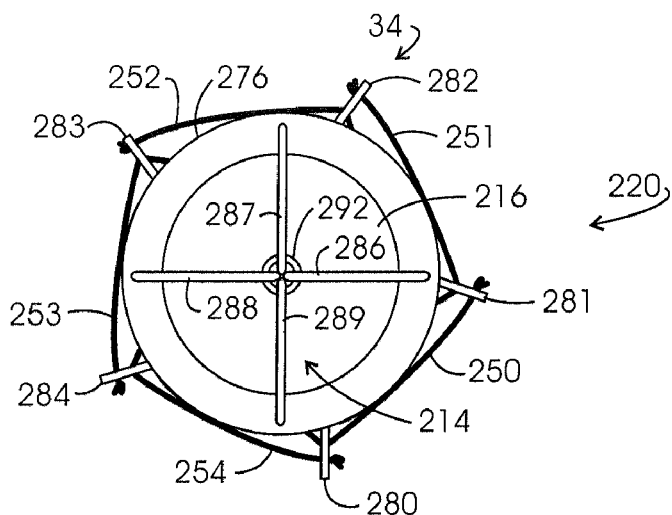
FIG. 5 is a front view of an instrument according to the invention showing a capture component in a retracted orientation.

Looking to FIG. 5, the initial orientation of cables 250-254 is revealed as well as the cruciform geometry of electrosurgically energized precursor assembly 214. These cables 250-254 assume the orientation shown during such time as the precursor assembly 214 is electrosurgically energized. Thus, in this orientation the cables 250-254 may be considered to be at an electrical ground status while arc inducing electrical power is applied to the assembly 214. Note that the cables 250-254 are drawn across the surface 276 of the forward region 34. These cables are drawn through as well as tied off with the eyelet components of five stainless steel capture basket defining leafs 280-284. In this regard, it might be noted that cable 250 extends through an aperture in leaf 280 and is tied off at the eyelet of a leaf 281. Similarly, cable 251 extends through an aperture within the eyelet of leaf 281 and is tied off at the eyelet of leaf 282; cable 252 extends through an aperture in the eyelet of leaf 282 and is tied off at the eyelet of leaf 283; cable 253 extends through an aperture within the eyelet of leaf 283 and is tied off at the eyelet of leaf 284; and cable 254 extends through an aperture in the eyelet of leaf 284 and is tied off at the eyelet of leaf 280.

Figure 6:
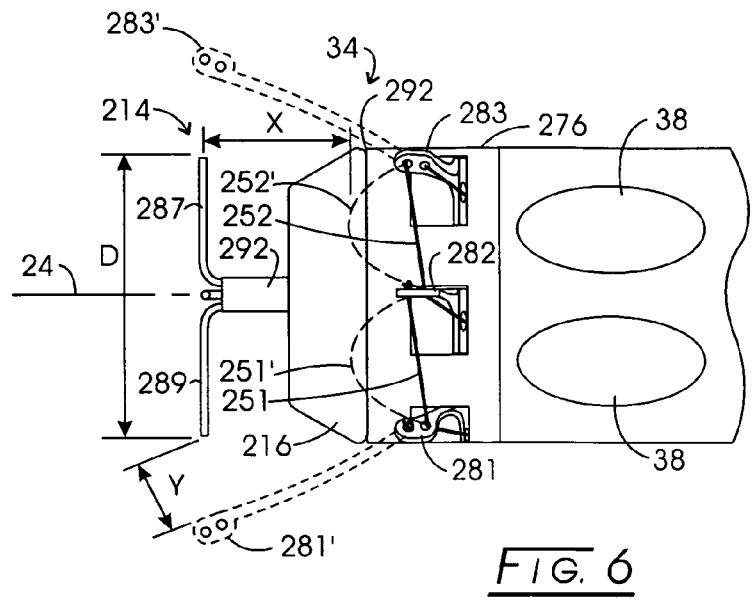
FIG. 6 is an enlarged view of the forward region of the delivery component of the instrument of FIG. 1.

Referring to FIG. 6, an enlarged view of forward region 34, surface 276 and capture component cables 251 and 252 is revealed. In normal usage, the cables as at 251 and 252, will have the orientation shown in solid line fashion which corresponds with the phantom location 244' of terminator component 244 as seen in FIG. 4. In the course of shipping and/or handling, however, the terminator component as at 244' may slide forwardly slightly and, thus before its use, should be returned to its initial orientation. If it is permitted to slide forwardly, then the cables have been observed to "slacken" forwardly as shown in FIG. 6 at 251' and 252'. During an energize/position mode described in connection with FIG. 1 in conjunction with foot pedal 98a, switch 63 and LED 106, precursor assembly 214 will be at a high voltage arc creating condition and the cables as at 251' and 252' will be essentially at ground. To prevent arc-over between the energized precursor assembly 214 and un-energized cables as at 251' and 252' individual electrosurgical electrodes of the assembly 214 should be spaced axially from the capture component cables, whether properly oriented or "slacken" a distance, x, which should be at least about 0.170 inch and preferably a distance about 0.190 inch. Thus, the individual electrodes of the assembly 214 as seen in FIG. 5 at 286-289 extend outwardly normally from instrument axis 24 and are straight. Note in this regard that to establish the spacing, x, as seen in FIG. 6, in addition to being disposed normally to axis 24, the precursor electrodes are seen to extend from a forwardly extending pedestal 292.

Figure 7A:
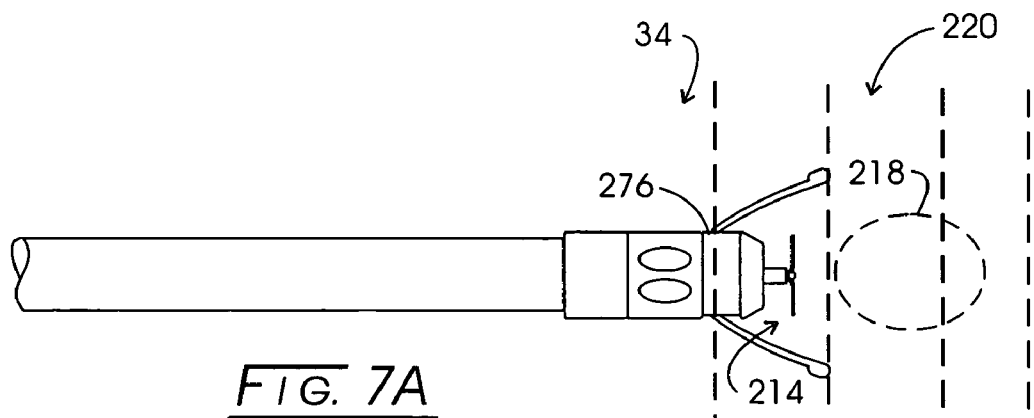
FIG. 7A-7C illustrate the sequence of a capture procedure.

Without more, a potential for arc-over phenomena to occur is present with respect to a de-energized precursor assembly 214 which essentially will be an electrical ground and an electrosurgically energized electrosurgical cutting leading portion established by cables 250-254, i.e., during the capture mode discussed in connection with FIG. 1. That mode commences with the depression of footswitch 98c following release of switch 98b and the depression of switch 98a. As noted above, switch 98a duplicates switch 62 on housing 18 and switch 64 on that housing duplicates switch 98c. With entry into the capture mode of operation, motor assembly 180 is energized and ears 160 and 162 commence to be driven by transfer assembly 210. As this occurs, drive member 270 (FIG. 4) is driven forwardly and the cables 250-254 pull terminator component 244 forwardly toward a cable stop 296. Leafs 280-284 will commence to be driven from their initial orientation as shown in FIG. 5 at a tip region angle of attack. That tip angle of attack is schematically represented in FIG. 7A, again in conjunction with symbolic target tissue volume 218. The angle of attack additionally is shown in phantom in FIG. 6 at 281' and 283'.

Returning to FIG. 4, as the five cables 250-254 are drawn forwardly while electrically excited, the terminator component 244 will encounter cable stop 296 at a location which is selected to establish the maximum effective "diametric extent" of opening as well as the overall length of the containment structure or cage generated by capture component 220. In this regard, that effective diametric extent may range from about 10 mm to about 40 mm. The term "effective" is utilized in connection with diametric extent inasmuch as the profile defined by the cables while excited emulates a pentagon.

Figure 8:
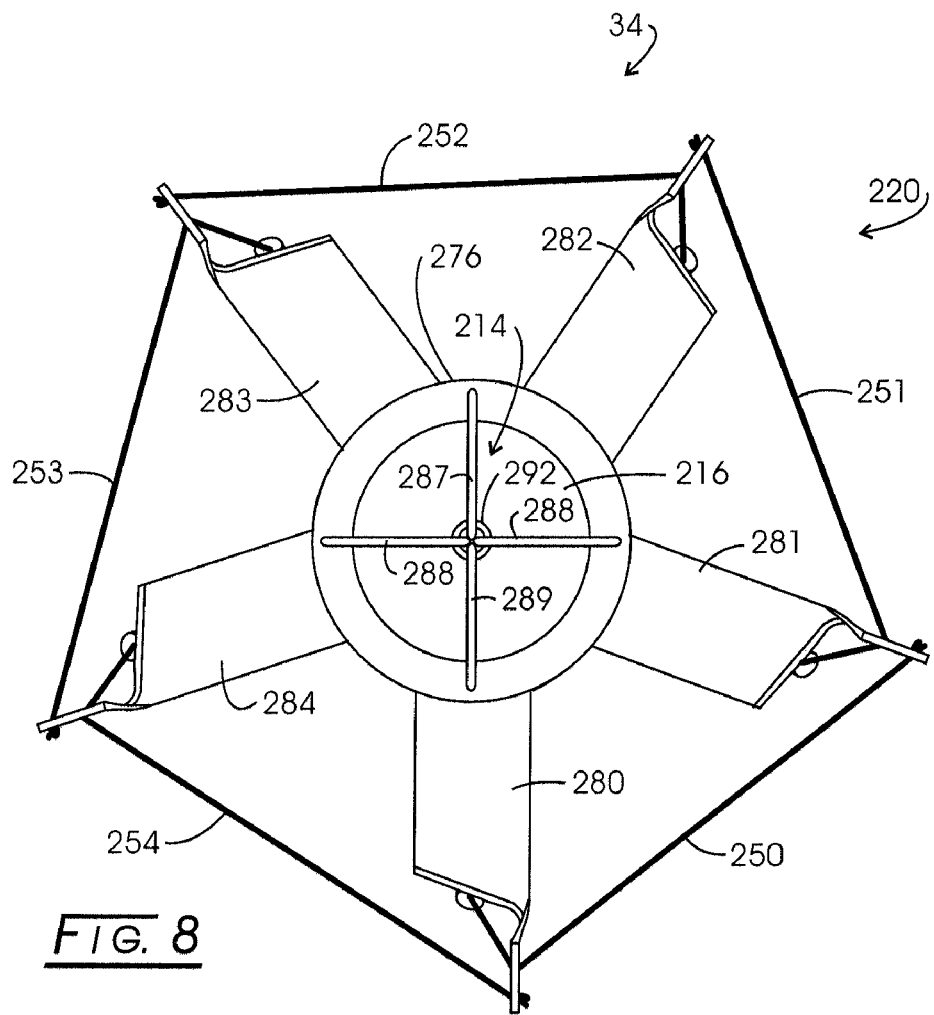
FIG. 8 is a front view of the instrument of FIG. 1 showing the capture component thereof at a stage in its deployment.
Figure 7B:
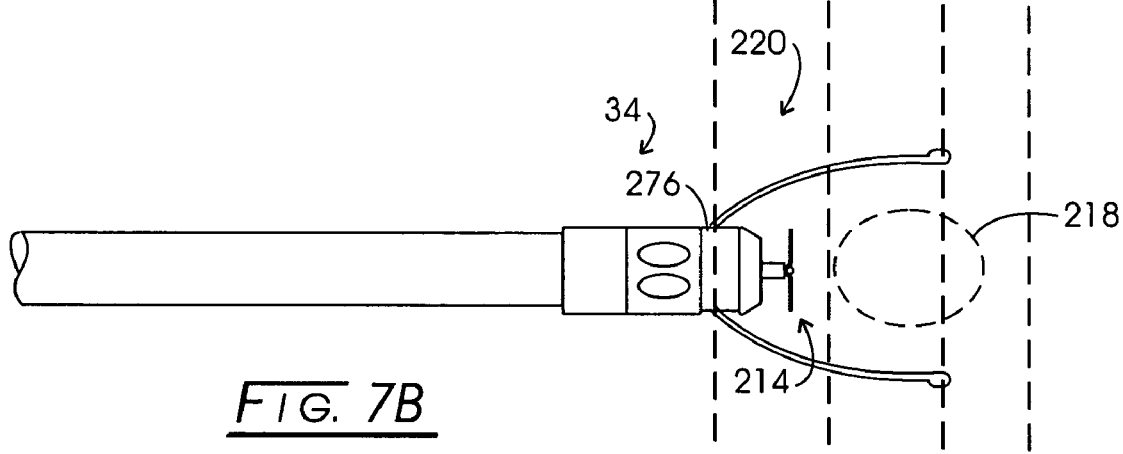
Figure 7C:
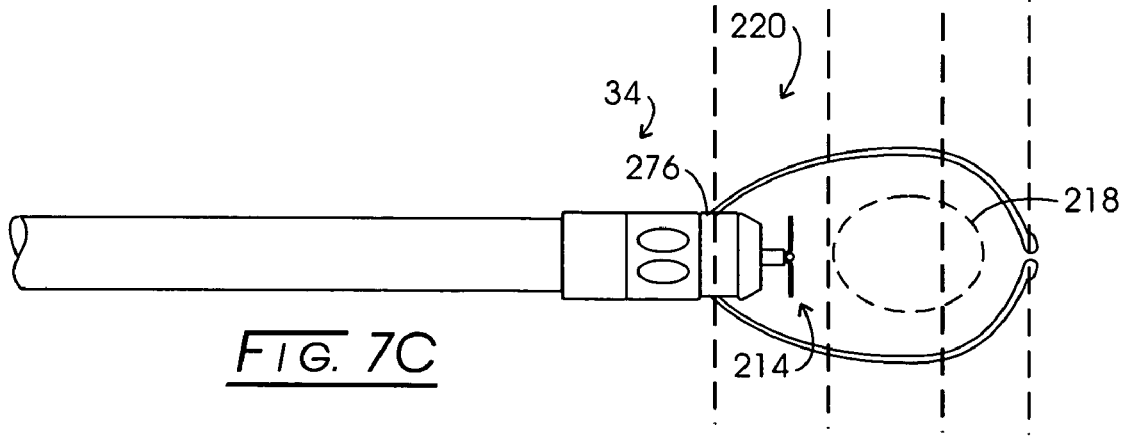

In general, cable stop collar 296 is located such that the sliding movement of terminator component 244 is blocked when capture component 220 achieves the intermediate position generally representing about one half of its longitudinal deployment at which position the noted maximum effective diametric extent is realized. That maximum effective diametric extent is represented schematically in FIG. 7B and is further represented in FIG. 8 where the pentagon emulation may be observed. The capturing performance of instrument 12 may be improved such that its use may extend to the recovery of very dense tissue by deriving a pursing stress on the cables which progressively increases toward a higher value generally established by blockage at cable stop 296. This progressive cable loading occurs as the terminator component 244 approaches stop 296 and, looking to FIG. 4, is implemented by the positioning of a resilient component present as a compression spring 298 located in abutment with cable stop collar 296. With the arrangement, the elliptical compression spring functions to modulate the extent of tension applied to the cable such that the leaf tip regions are more gradually vectored inwardly toward axis 24 at the commencement of pursing activity. A more detailed description of the performance of spring 298 and the capture component 220 is provided in application for U.S. patent Ser. No. 10/630,336 entitled "Electrosurgical Method and Apparatus With Dense Tissue Recovery Capacity", by Philip E. Eggers, now U.S. Pat. No. 6,955,653, issued 18 Oct. 2005. Energization of motor assembly 180 continues until drive member 270 abuttably engages capture stop component 274 (FIG. 4). At that point in time, a resultant inductive spike is created which shuts down electrosurgical excitation of cables 250-254 and causes the motor assembly 180 to reverse and return yoke 210 (FIG. 3) to its "home" position. Capture component 220 will have been maneuvered at pursing angles of attack until the noted de-energization of motor assembly 180 to assume a profile symbolically represented in FIGS. 4 and 7C.

Returning to FIG. 6, during the laterally outwardly expanding locus of travel of the leafs and cables the electrosurgically energized capture component leading edge will pass a distance, y, from the tips of the now electrically grounded precursor electrode components 286-289. The minimum distance for spacing, y, is at least about 0.170 inch and preferably it is about 0.190 inch. FIG. 6 also reveals that the oppositely disposed precursor components as, for instance, at 287 and 289, when combined show a maximum width, D, which is less than the corresponding maximum widthwise extent of surface 276. For the instant embodiment that width is a diameter. For example, where the diameter of probe forward portion 34 at surface 276 is about 0.25 inch, the corresponding value for, D, will be about 0.24 inch.

Figure 9:
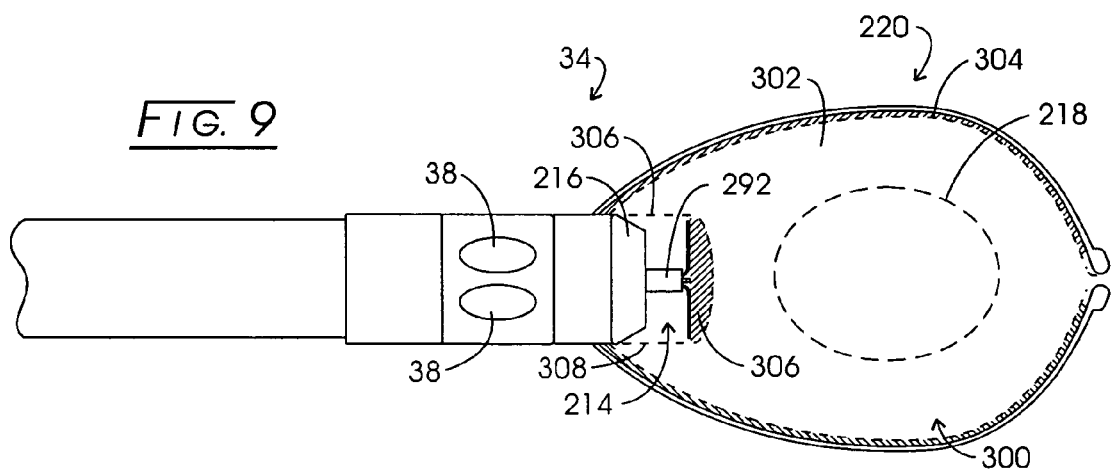
FIG. 9 is a side view of the forward region of the instrument of FIG. 1 showing artifact regions.

Looking to FIG. 9, target tissue volume 218 reappears in conjunction with a full capture orientation for the capture component 220. The figure reveals that the biopsy sample in total as represented generally at 300 will include what may be considered surrounding healthy tissue 302. That tissue 302, by virtue of the electrosurgical cutting activity of the cables 250-254 will exhibit a perimeter thermal artifact represented at shading 304 which is well spaced from the target tissue volume 218. Additionally, precursor assembly 214 may dwell in an energized state to produce a zone artifact represented in the shaded region 306. In this regard, note additionally that the access channel which is cut is represented at dashed lines 308.

It is a characteristic of system 10 that the biopsy sample as at 300 will be larger in width dimension than the precursor length, D. Thus, consideration must be made as to how the larger sample is to be retrieved through the accessing channel without invoking a crush artifact. The cruciform geometry of the precursor assembly 214 is advantageous in that respect. Looking to FIG. 10, it may be observed that electrode component 286 provides oppositely disposed tissue cuts 286a and 286b; electrode component 287 creates cut tissue surfaces 287a and 287b; electrode component 288 creates oppositely disposed cut tissue surfaces 288a and 288b; and electrode component 289 creates oppositely disposed cut tissue surfaces 289a and 289b. Each of the surfaces 286a, 286b-289a, 289b exhibits a length of, D/2. When these surfaces are spread apart by the capture component 220 with its associated tissue sample 300 during removal of the sample, the circumference of incision, Ci, may be computed as follows:

$$Ci = 8 * \frac{D}{2} = 4D$$

The corresponding diameter or length of the incised pathway, Di may be computed as follows:

$$Di = \frac{Ci}{\pi} = \frac{4D}{\pi} = 1.27D$$

Figure 11:
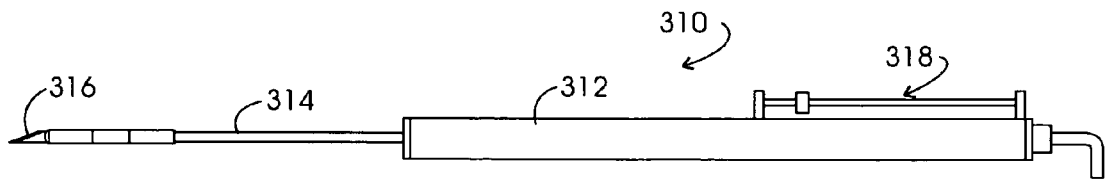
FIG. 11 is a side view of a force measuring gauge.

The majority of commercially available breast biopsying systems employ a surgically sharpened mechanical tip for the positioning of the sampling instrument with respect to a target tissue volume. Mechanical, surgically sharp precursor assemblies may be employed with systems as at 10, however, to avoid arc-over phenomena, these mechanical tips should be not only sharp, but electrically insulative. As part of the study looking to the development of a surgically sharp mechanical precursor assembly, tests were carried out with a variety of tip structures measuring the force required to insert such tip structures through the breast region of in vivo porcine tissue. As a preliminary procedure to attempts at tip insertion, the skin first was cut with a number 11 scalpel blade to a width of 7-8 mm and a depth of 8 mm. Force required for penetrating the instrument tip was measured by a force gauge of a spring based variety marketed as a model no. 719 by McMaster-Carr Supply Company having a place of business in Cleveland, Ohio. Such a device is illustrated in FIG. 11 in general at 310. Looking to the figure, a handle 312 is seen to slidably support a penetration shaft 314 which, in turn, supports a blade to be tested 316. A force readout assembly is represented in general at 318. Test results are compiled in Table 1 hereof. Looking to the table, a polymeric bladed tip was tested. This blade was formed as a triangle and fabricated from polyether ether ketone (PEEK) and had a tip angle of about 60°. Three attempts were made to penetrate tissue with this tip, all of which failed and were terminated at readings of between 9.0 and 9.1 pounds.

Figure 12:
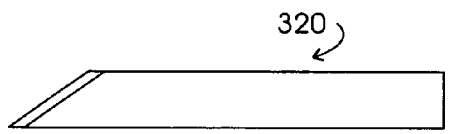
FIG. 12 is a side view of a zirconia surgical blade having a 45° included angle.
Figure 13:
FIG. 13 is a side view of a zirconia surgical cutting blade having an included angle of 25°.

Next, a polymeric tip configuration of a trocar shape with three sides was fabricated of the noted PEEK material. The included angle of the tip was about 60°. This tip was considered to have failed, having instrument readouts of 9.0, 9.1 and 7.6 pounds. Next in the listing is a commercial breast biopsy product marketed by Ethicon Endo-Surgery, Inc. of Cincinnati, Ohio under the trade designation Mammotome® as an MST-8 eight gauge probe having a bladed tip formed of stainless steel. The tip had an included angle of 58°. Two successful attempts were made with this eight gauge probe having an average penetration force readout of 1.25 pounds. Ceramic blades were tested, in particular, blades formed of a zirconia marketed by Specialty Blades, Inc. of Staunton, Va. One blade having an included tip angle of 45° represented in general at 320 in FIG. 12 is seen to have penetrated tissue with an average force of 0.56 pounds. Another blade formed of such a zirconia material having an included angle at the tip of 25° as shown in general at 322 in FIG. 13 performed with an average insertion force of 0.38 pounds.

Finally, an electrosurgically excited precursor as, for example, described in U.S. Pat. No. 6,471,659 was tested.

TABLE 1

| Tip Configuration | Cutting Tip Material | Included Angle of Tip | Probe Number | Measured Insertion Force | Was Pre-Cut Tissue Penetrated by Probe Tip? | Comments |
|---|---|---|---|---|---|---|
| Polymeric bladed tip | PEEK | ~60 degrees | 4446566-188 | Stopped trying at 9.1 lbs (4.1 KG) | No | Attempted with 3 different probes |
| | | | 525084B-3 | Stopped trying at 9.0 lbs (4.1 KG) | No | |
| | | | 510064A-257 | Stopped trying at 9.0 lbs (4.1 KG) | No | |
| Polymeric trocar tip | PEEK | 3 sides ~60 degrees | 525084B-83 | Stopped trying at 7.6 lbs (3.5 KG) | No | Attempted with 3 different probes |
| | | | 525084B-86 | Stopped trying at 9.0 lbs (4.1 Kg) | No | |
| | | | 525084B-137 | Stopped trying at 9.1 lbs (4.1 Kg) | No | |
| Mammotome MST-8 8 gauge Probe | Stainless Steel | 58 degrees | $1^{st}$ test | 1.1 lbs (0.50 Kg) | Yes | New, freshly removed from package |
| | | | $2^{nd}$ test | 1.4 lbs (0.64 Kg) | Yes | 2 uses of same Probe, smooth cut |
| Ceramic blade in holder, made by Specialty Blades, Inc. (Staunton VA) Off-the-shelf blades | Zirconia | 45 degrees | Blade 1 | 0.63 lbs (0.28 Kg) | Yes | Very smooth, easy advancement. |
| | | | Blade 2 | 0.50 lbs (0.23 Kg) | Yes | Blade sharpened on one side only |
| | | | Blade 3 | 0.56 lbs (0.25 Kg) | Yes | |
| Ceramic blade in holder, made by Specialty Blades, Inc. (Staunton VA) Off-the-shelf blades | Zirconia (0.020" thick) | 25 degrees | Blade 1 | 0.25 lbs (0.11 Kg) | Yes | Very smooth, easy advancement |
| | | | Blade 2 | 0.50 lbs (0.23 Kg) | Yes | Blade sharpened on one side only |
| | | | Blade 3 | 0.40 lbs (0.18 Kg) | Yes | |
| En-Bloc Probe with Straight Wire 4-Branch Precursor Electrode | SS304 | .0.055" Height | 31705-10 | 1.5 lbs (0.68 Kg) | Yes | Retractor used to position Probe In tissue. |

Referring to FIGS. 14-17, a precursor assembly is represented generally at 330. Assembly 330 is electrically insulative and is seen to be formed with a blade represented generally at 332 which preferably is formed with a ceramic material such as a zirconia. As seen in FIGS. 15 and 17, blade 332 is formed with oppositely disposed surfaces having a generally triangular periphery and mutually aligned with instrument axis 24. Blade 332 has a base 336 as seen in FIGS. 14 and 16 which is intended to be affixed adjacent the probe or delivery member distal end or tip and which has a length which is co-extensive with the delivery member or probe widthwise extent. Where the probe is configured with a circular cross section at its tip, then that widthwise extent corresponds with its diameter. The remaining periphery of blade 332 is configured having surgically sharp edges 338 and 339 which extend from the base 336 to a blade apex 340 aligned with axis 24. Blade 332 is seen supported by an electrically insulative polymeric support represented generally at 342. Support 342 is configured with a mounting post 344 as seen in FIGS. 14, 16 and 17 which is extensible within the distal tip of the probe instrument. Integrally formed with the post 344 is an electrically insulative tissue spreader represented generally at 346 having oppositely disposed tapering or conical surfaces 348 and 349 which extend from adjacency with the base 336 to adjacency with respective surfaces 334 and 335 to spreader apexes shown respectively at 352 and 353 which are aligned with axis 24. As seen particularly in FIG. 17, the spreader apexes 352 and 353 are located in adjacency with respective blade surfaces 334 and 335 at an axially aligned location below the blade apex 340.

Figure 18:
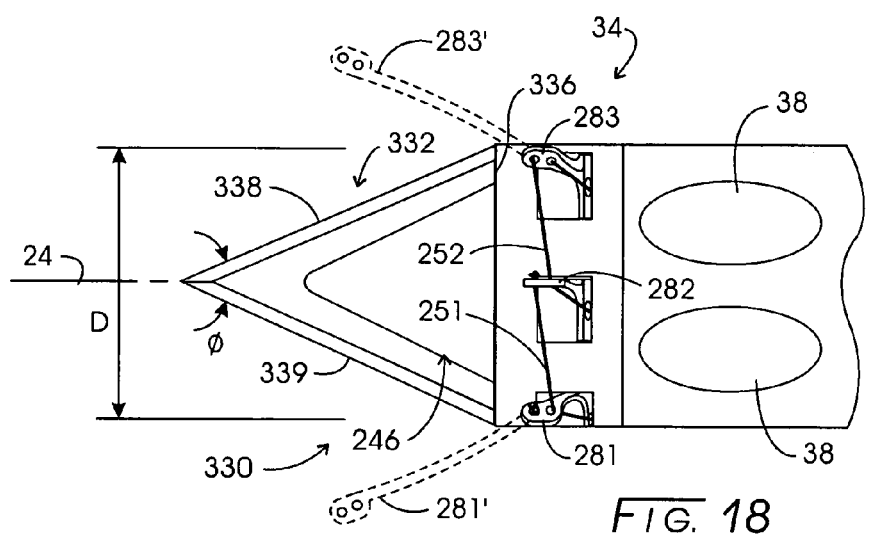
FIG. 18 is a partial view of the forward region of the instrument of FIG. 1 in combination with the precursor assembly described in FIGS. 14-17.

Looking to FIG. 18, instrument forward region 34 is reproduced in the manner of FIG. 6 with the same identifying numeration. However, for the arrangement of this figure the alumina tip component 216 as shown in FIG. 6 has been removed and thus the blade 332 base 336 is located further axially inwardly with respect to the capture component leads and cables. In the figure, base 336 is seen to have a dimension, D, and an analysis of the circumference of incision as provided above may be carried out. In this regard, the circumference of incision, Ci may be established as follows:

$$Ci = 2D$$

The incised pathway diameter, Di, may be developed as follows:

$$Di = \frac{Ci}{\pi} = 2\frac{D}{\pi} = 0.64D$$

Figure 19:
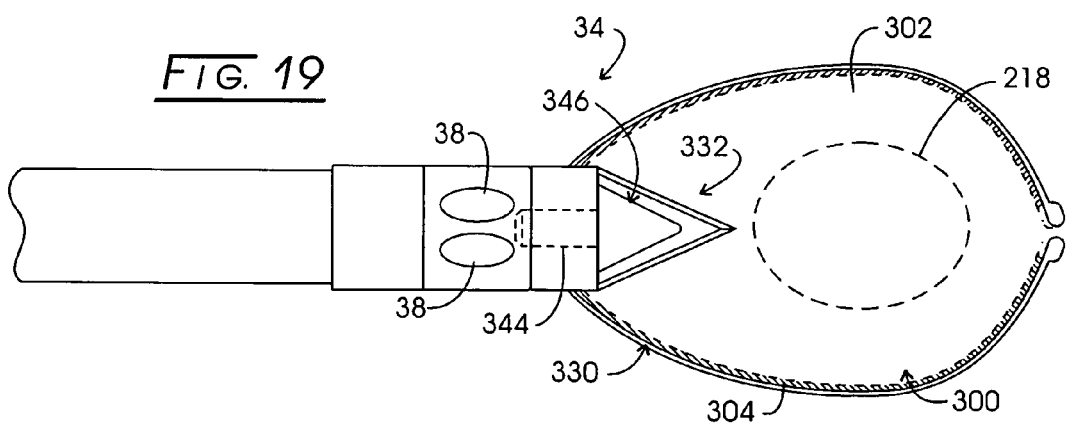
FIG. 19 is a view of the forward region of the instrument of FIG. 18 showing a perimeter thermal artifact.

Looking to FIG. 19, tip region 34 is presented in the manner of FIG. 9, again with the removal of alumina tip component 216 and electrosurgical precursor assembly 214. The relative orientation of surgical blade 332 is illustrated with respect to target tissue volume 218. Biopsy sample 300 is seen to exhibit the same peripheral thermal artifact 304 which is of no pathology moment and no zone of artifact associated with the precursor assembly is present. However, when employing this mechanical precursor approach, consideration is made as to the available size of sample to be retrieved to avoid crush artifact phenomena.

Preferably, blade edges as at 338 and 339 will equal or approach the Bard-Parker gold standard of sharpness. In general, the value of, D, will be in a range from about 3 mm to about 10 mm and preferably within a range of from about 5 mm to about 7 mm. This base width also applies to trocar-type tips as are described later herein. Also, the included angle, ø, will be in a range of from about 30° to about 70° and preferably within a range of from about 40° to about 55°.

Referring to FIGS. 20-23, another precursor assembly is represented generally at 360. Assembly 360 incorporates a triangular shaped blade represented generally at 362 formed with electrically insulative materials and preferably a ceramic material, for example, such as a zirconia. Similar to blade 332, blade 362 is configured with oppositely disposed surfaces seen in FIGS. 21 and 23 at 364 and 365 having a generally triangular periphery and symmetrically disposed or aligned about the instrument axis as at 24. Blade 362 incorporates a base seen in FIGS. 20, 22 and 23 which is mounted in the manner described in connection with FIGS. 18 and 19 at the distal tip of a delivery structure, that base also being coextensive with the widthwise extent of that structure which generally will be a diameter. The periphery of blade 362 exhibits surgically sharp edges 368 and 369 which extend from the base to a principal blade apex 370 aligned with the instrument axis 24.

Principal blade 362 is operatively associated with a second electrically insulative blade represented generally at 372. Blade 372 preferably is formed with a ceramic material, for example, a zirconia material and, as represented in FIGS. 21 and 22 is configured with oppositely positioned surfaces 374 and 375 disposed normally to surface 364 and which exhibit a generally right triangular periphery having a base 376 coplanar with base 366 and a hypotenuse related surgically sharp edge 378 extending from the base to an apex 380 adjacent surface 364. Note that apex 380 is inwardly disposed from principal blade apex 370.

Assembly 360 further includes a third electrically insulative blade represented generally at 382. Blade 382 is formed of a ceramic material such as a zirconia and is seen in FIG. 21 to have opposite surfaces 384 and 385 aligned with and symmetrically disposed about instrument axis 24 and located oppositely from blade 372 to define a cruciform or quadrature geometry symmetrically disposed about axis 24. Blade 382 is configured identically with blade 372 having a generally right triangular periphery with a base seen in FIG. 23 at 386 which is coplanar with base 366 and a hypotenuse related surgically sharp edge 388 extending to an apex seen in FIG. 23 at 390. Apex 390 is aligned with apex 380 and is located below principal apex 370. Blades 362, 372 and 382 are retained by an electrically insulative polymeric support represented generally at 392. Support 392 is configured with a mounting post 394 and four integrally formed tissue spreaders 396-399 tapered to an apex, one of which is revealed in FIG. 20 at 400. Note that all four of these apexes as at 400, are located adjacent an associated blade 362 surface, below blade apexes 380 and 390.

Figure 10:
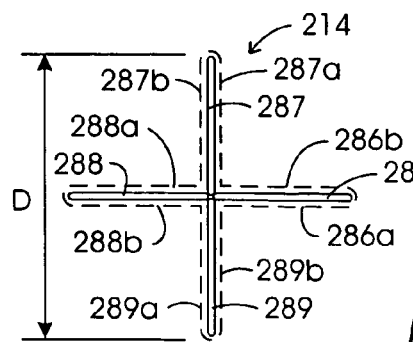
FIG. 10 is a front view of a cruciform type precursor electrode and further illustrating cut tissue surfaces.

With the above arrangement, as described in connection with FIG. 10, a circumference of incision, Ci, becomes 4D and the corresponding incised pathway diameter, Di, becomes 1.27D.

The cruciform or quadrature geometry also can be implemented utilizing four right triangular electrically insulative blades to derive the same incise pathway diameter, Di. Preferably, these blades are formed of a ceramic material such as a zirconia. Looking to FIGS. 24 and 25, a precursor assembly is represented generally at 410. Assembly 410 is configured with four electrically insulative blades represented generally at 412-415, each having a base as shown respectively at 416-419 arranged in coplanar fashion at the tip of the probe or delivery member. From that base and delivery member tip profile, each blade 412-415 is configured with a hypotenuse related surgical cutting edge shown respectively at 420-423 which extend to a common apex 424. Blades 412-415 are affixed in their quadrature geometry by an electrically insulative polymeric support represented generally at 426. Support 426 is configured with a mounting post 428 (FIG. 24) and four integrally formed polymeric tissue spreader components 430-433, each having a conical surface extending to an apex located axially inwardly from blade apex 424. One such spreader apex is seen in FIG. 24 at 434.

The precursor assembly also may be configured with three electrically insulative blades symmetrically disposed about the instrument axis. As before, it is preferred that these blades be formed of a ceramic material, for example, a zirconia material. Referring to FIGS. 26 and 27, such a precursor assembly is represented generally at 440 incorporating three such blades represented generally at 442-444. Blades 442-

444 are configured with a generally right triangular periphery with respective coplanar bases 446-448 as seen in FIG. 27. These coplanar bases are intended to be located against the surface of the probe or delivery member tip and each is formed with a surgically sharp hypotenuse related cutting edge shown respectively at 450-452. These cutting edges extend to a common blade apex seen in FIG. 27 at 454. Blades 442-444 are affixed to an electrically insulative polymeric support represented generally at 456. Support 456 incorporates a mounting post 458 (FIG. 27) and four integrally formed tissue spreader components 460-462. Spreader components 460-462 extend from the common base plane of the blade bases 446-448 to a spreader apex located inwardly from the blade apex 454. In this regard, FIG. 27 reveals the conical tissue spreader surfaces 460 and 461 extending to respective apexes 464 and 465. These apexes are aligned in adjacency with the instrument axis 24.

Now looking to the circumference of incision developed with precursor assembly 440, it may be observed that each blade will make an incision of D-2 to value. Accordingly, the circumference of incision, Ci may be expressed as follows:

$$Ci = 6 * \frac{D}{2} = 3D$$

Accordingly, the diameter or length of the incised pathway may be expressed as follows:

$$Di = \frac{Ci}{\pi} = \frac{3D}{\pi} = 0.95D$$

Solid or trocar-type precursor assemblies also may be deployed with the probe or delivery components of the invention. Looking to FIGS. 28 and 29, a four sided precursor assembly is represented generally at 470. Assembly 470 is formed of an electrically insulative material, for instance, a ceramic material such as a zirconia. The assembly 470 is a unitary solid cutting member with a base 472 of square profile from which depends an integrally formed mounting post 474. Assembly 470 has four sides 476-479 which extend to an apex 480 aligned with axis 24 and which combine to define four surgically sharp cutting edges 482-485.

Now considering the circumference of incision derived with these cutting edges, the following expression of obtains:

$$Ci=4*0.707D=2.83D$$

The corresponding incised pathway diameter becomes:

$$Di = \frac{Ci}{\pi} = \frac{2.83D}{\pi} = 0.90D$$

The trocar type precursor assembly also may be provided as a unitary solid electrically insulative cutting member similar to assembly 470 but having three sides. Looking to FIG. 30, an end view of such a device is represented generally at 490. Assembly 490 exhibits a triangular base from which extends three sides 492-494 to define three surgically sharpened cutting edges 496-498 which extend to an apex 500. Not shown in the figure is a mounting post similar to that illustrated in FIG. 28 at 474.

The circumference of incision of assembly 490 may be expressed as follows:

$$Ci=3*(0.867D)=2.6D$$

The corresponding incised pathway diameter then may be expressed as follows:

$$Di = \frac{Ci}{\pi} = \frac{2.6D}{\pi} = 0.83D$$

A hybrid form of precursor assembly is represented generally at 510 in FIG. 31. Assembly 510 is configured with a triangular shaped metal blade represented generally at 512. It is formed, for example, of a stainless steel, the blade 512 is coated with an electrically insulative material such as diamond and is configured with a base at 514 from which extend surgically sharpened cutting edges 516 and 517. Edges 516 and 517 converge at an apex 518 aligned with instrument axis 24. The electrically insulative coating is not present at oppositely spaced blade regions 520 and 521. Blade 512 is fixed to an electrically insulative support assembly represented generally at 524. Assembly 524 may be formed of an injection molded plastic, e.g., polycarbonate and is configured with a mounting post 526 and integrally formed conically surfaced tissue spreading components 528 and 529 which extend to a oppositely disposed spreader apexes, one of which is seen at 530 spaced inwardly from blade apex 518. Not seen in the figure is a channel extending through the mounting post 526 providing for the delivery of electrosurgical current to blade 512. Accordingly, the regions 520 and 521 are located to meet the spacing criteria discussed above in connection with FIG. 6.

Since certain changes may be made in the above apparatus without departing from the scope of the invention herein involved, it is intended that all matter contained in the above description or shown in the accompanying drawings shall be interpreted as illustrative and not in a limiting sense.

The invention claimed is:
1. Apparatus for retrieving a tissue volume, comprising:
a delivery assembly with a delivery member having a member exterior surface surmounting an interior channel assembly extending from a proximal portion along an axis to a forward region having a distal end supporting an electrically insulative heat resistant forward surface and said member exhibiting a member widthwise extent;
a capture component positioned at said delivery member forward region, having a forward portion extending to a forwardly disposed tip region with a pursing cable assembly energizable to define an electrosurgical cutting leading portion, said cable assembly including tensionable cables extending from said forward portion at a deployment location thence along said interior channel assembly to a cable terminator, said forward portion being drivably extendable from an initial position, wherein portions of said cables extend about said member exterior surface at said deployment location, outwardly from said exterior surface and forwardly at a tip region angle of attack, while creating an electrosurgical arc, toward an intermediate position while drawing said cables along a laterally outwardly expanding locus of travel, said electrosurgical cutting leading portion defining a cutting profile of maximum effective diametric extent in correspondence with said intermediate position, and subsequently being drivably extendable while being drawn in contraction toward said axis at tip region inwardly directed pursing angles of attack by pursing stress at said cable assembly to a capture position;

a precursor assembly comprised of two or more straight electrosurgical electrodes, each extending generally normally to and from the vicinity of said longitudinal axis to an electrode tip located a distance from said axis less than one-half said member widthwise extent and spaced axially forwardly from said portions of cables a distance, x, effective to avoid arc-over from said electrosurgical electrodes to said positions of cables extending about said member exterior surface when said precursor assembly is electrosurgically excited and said pursing cable assembly is not electrosurgically excited; and a control assembly actuatable to energize and de-energize said precursor electrodes having a drive portion in driving engagement with said capture component and actuatable to drive said capture component forward portion from said initial position into said capture position while effecting the electrosurgical energization thereof and de-energization of said pursing cable assembly.

2. The apparatus of claim 1 in which:
said distance, x, is at least about 0.170 inch.

3. The apparatus of claim 2 in which:
said distance, x, is about 0.190 inch.

4. The apparatus of claim 1 in which:
said delivery member widthwise extent is a diameter about said axis of about 0.25 inch; and
said precursor electrode tip is located at a radius of about 0.12 inch from said axis.

5. The apparatus of claim 1 in which:
said capture component pursing cable cutting leading portion locus of travel is spaced from each said precursor assembly electrode tip when said pursing cable assembly is energized and said precursor assembly is not electrosurgically excited, a distance, y, effective to avoid arc-over.

6. The apparatus of claim 5 in which:
said distance, y, is at least about 0.170 inch.

7. The apparatus of claim 5 in which:
said distance, y, is about 0.190 inch.

* * * * *